(12) United States Patent
Elledge et al.

(10) Patent No.: US 6,376,192 B1
(45) Date of Patent: Apr. 23, 2002

(54) METHOD FOR SCREENING OF DNA LIBRARIES AND GENERATION OF RECOMBINANT DNA CONSTRUCTS

(75) Inventors: Stephen J. Elledge, Houston; Pumin Zhang, Pearland; Mamie Li, Houston, all of TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/724,934

(22) Filed: Nov. 28, 2000

(51) Int. Cl.$^7$ .......................... C12Q 1/68; C12N 15/74
(52) U.S. Cl. .......................... 435/6; 435/477
(58) Field of Search .............................. 435/6

(56) References Cited

U.S. PATENT DOCUMENTS

| | | | |
|---|---|---|---|
| 6,069,010 A | 5/2000 | Choi | 435/477 |
| 6,090,629 A | 7/2000 | Woychik | 435/472 |

FOREIGN PATENT DOCUMENTS

| | | | | |
|---|---|---|---|---|
| US | WO 98/37175 | 8/1998 | ............ | C12N/5/00 |
| US | WO 99/23238 | 5/1999 | ............ | C12N/15/90 |
| US | WO 99/40212 | 8/1999 | ............ | C12N/15/85 |

OTHER PUBLICATIONS

Chua and Oliver, "Intramolecular homologous recombination of linearized plasmids in *Escherichia coli* K12," Mol. Gen. Genet. 232:199–205, 1992.

Chua, et al., "Expression of the recA gene in recombination–deficient (rec–) strains of *Escherichia coli*," Biochimie, 75: 775–83, 1993.

Elledge, et al., "lamda–YES: A multifunctional cDNA expression vector for the isolation of genes by complementation of yeast and *Escherichia coli* mutations," Proc. Natl. Acad. Sci. USA, 88:1731–35, 1991.

Elledge, et al., "Novel Method for the Generation of Recombinant DNA Constructs Without the Use of Restriction Enzymes," Baylor College of Medicine Website, Apr. 17, 1998.

Liu, et al., "The univector plasmid–fusion system, a method for rapid construction of recombinant DNA without restriction enzymes," Current Biology, 8:1300–09, 1998.

Poteete, et al., "Roles of RuvC and RecG in Phage lamda Red–Mediated Recombination," Journal of Bacteriology, 181(17):5402–08, 1999.

Winans, et al., "Site–Directed Insertion and Deletion Mutagenisis with Cloned Fragments in *Escherichia coli*," Journal of Bacteriology, 161(3):1219–21, 1985.

Yokochi, et al., "Evidence for Conservative (Two–Progeny) DNA Double–Strand Break Repair," Genetics, 139:5–17, 1995.

Yu, et al., "An efficient recombination system for chromosome engineering in *Escherichia coli*," Proc. Natl. Acad. Sci., 97(11): 5978–83, 2000.

Zakhartchouk, et al., "Construction and Characterization of E3–Deleted Bovine Adenovirus Type 3 Expressing Full–Length and Truncated Form of Bovine Herpesvirus Type 1 Glycoprotein gD1," Virology, 250:220–29, 1998.

*Primary Examiner*—Kenneth R. Horlick
*Assistant Examiner*—Teresa Strzelecka
(74) *Attorney, Agent, or Firm*—Vinson & Elkins

(57) ABSTRACT

A method of DNA library screening includes homologous recombination in *E. coli* utilizing lambda phage recombination functions. Inserting a positive selection marker such as antibiotic resistance into the target sequence by homologous recombination facilitates isolation of target sequences and requires only about 58–100 base pairs of total homology, thus allowing the use of synthetic fragments of DNA for targeting. DNA vector is designed for genomic library construction that features a novel genetic selection for inserts, automatic subcloning of isolated genomic clones and the presence of a negative selection marker adjacent to the genomic inserts to facilitate later gene targeting.

51 Claims, 11 Drawing Sheets

METHOD FOR SCREENING OF DNA LIBRARIES AND GENERATION OF RECOMBINANT DNA CONSTRUCTS

BACKGROUND

1. Field of the Invention

The present invention is related to the field of molecular biology and more particularly to the field of screening DNA libraries such as genomic and cDNA libraries to isolate a desired gene, and to the field of construction of targeting vectors for use in targeting a chromosomal gene, wherein the targeting vectors are constructed utilizing homologous recombination in E. coli.

2. Description of Related Art

The development of technologies for targeted gene disruption in mouse embryonic stem cells (ES cells) has profoundly shaped biological research and the technique is now routinely used in laboratories. As the human genome project comes to completion and the mouse genome project comes to center stage, the demand for knockout mice is certain to increase dramatically in hopes of defining functions of the large volume of genes discovered by whole genome sequencing. The production of knockout mice, however, is still a time consuming process. A number of molecular manipulations must be performed to build a knockout construct to target the gene of interest in ES cells. First, genomic clones of the gene must be isolated and characterized. Secondly, a knockout construct is built in which a positive selection marker (usually the neomycin or puromycin resistant gene) is flanked by genomic sequences of several kilobases and a negative selection marker (usually the thymidine kinase of herpes virus) is placed at one end followed by plasmid backbone. These manipulations can be a rate-limiting step for generation of a knockout mouse and can often inhibit the decision to make a genetically altered mouse.

To identify a genomic region of interest, prior methods used plaque hybridization using a radioactive probe, usually a cDNA from the gene of interest, to identify the lambda phage containing the homologous genomic region of interest. This is labor intensive requiring multiple rounds of purification to identify just a few homologous clones. In addition, since it is based on hybridization, it often can pick up related sequences such as psuedo-genes that have related but not strictly identical DNA sequences. Similarly, the methods to identify full length cDNAs from libraries also require plaque screens using hybridization and radioactive probes and multiple rounds of screening. Thus, the methods previously used to identify phage containing homologous genomic DNA and cDNA are both laborious and time consuming.

It was contemplated by the present inventors that the described processes may be simplified by taking advantage of homologous recombination in E. coli. Several recombination pathways have been identified in E. coli with the RecBCD pathway playing a major role in the double-strand break repair pathway. RecBCD encodes a helicase and a nuclease that unwind and degrade DNA to generate 3'single-stranded tails utilized by the RecA protein for invasion to initiate the recombination process. However, homologous recombination efficiency between a linear piece of DNA and the host chromosome is very low in E.coli cells that express wildtype RecBCD because the introduced linear DNA molecules are degraded rather efficiently before recombination has had a chance to proceed. It has been found that a short sequence, 5'-GCTGGTGG-3', called a Chi site, can stimulate homologous recombination, as this short sequence is inhibitory to the nuclease function of RecBCD. In order for a linear DNA molecule to recombine with the host chromosome or a resident plasmid, either RecBCD must be inactivated or Chi sites must be present on the linear DNA. In a strain with a mutant RecBCD (JC8679[ ], for example), linear DNA can recombine with a host chromosome or plasmid with modest efficiency. Initial attempts by the inventors to utilize the mutant RecBCD strain were not ideal, however, because the recombination efficiency was too low to screen for single copy genes within the complexity of the mouse genome. There is still a need, therefore, for simple methods of screening a genomic library and constructing targeting vectors for use in the knock out of genes of interest in mammalian species, such as mice.

SUMMARY

The present disclosure overcomes drawbacks in the prior art by providing compositions and methods that simplify the screening of DNA libraries to select genes of interest through the use of homologous recombination in E. coli. A particular advantage of the present invention is that one can identify and select a gene of interest based on only about 60–100 bases of homology and can at the same time modify that gene fragment for use as a knockout targeting vector, for example. The invention is particularly useful in the screening of large libraries such as mammalian genomic libraries for the isolation of genomic copies of mammalian genes, for example, and in the construction of knockout targeting vectors. The invention is also useful for the screening of any DNA target, including cDNA libraries, BAC libraries, or cosmid libraries for various applications such as to extend partial sequences or to fill in sequence gaps in such libraries or genes within those libraries.

The advantages of the present compositions and methods arise from the ability to select a gene of interest from a DNA library based on the homology required for homologous recombination and simultaneously insert a positive selection marker into that gene so that only the targeted clones survive in the selection media. Using the compositions and methods described herein, one is thus able to isolate nucleic acid segments or clones of interest from a nucleic acid library via homologous recombination using regions of homology as small as about 60–100 base pairs (bp). By this description of the homology being about 60–100 base pairs, it is understood that this represents a minimum amount of sequence homology of about 56, 58 or 60 base pairs, but that much larger regions may be used, such as 200–500 or even several thousand bases or more of homology as desired by the practitioner. It is also understood that the regions of targeting homology are separated by the selection marker so that, in certain embodiments approximately one half the region of homology will appear at each end of the selectable marker region in the targeting construct. In certain preferred embodiments, then one may use regions of homology of about 26, 28, 30, 40, 50, 60, 75 or even 100 bases for each targeting region, making a total of about 50 or 60 to 200 bases of total homology.

Once the clones are selected and isolated, they can then be sequenced and used to construct complete genes or cDNA sequences, to fill gaps in sequence data, or even for genomic walking to obtain further sequence data. Furthermore, the compositions and methods of the present disclosure allow the screening of a library and production of a finished genetic targeting construct in less than a week, in contrast to months of work that are often required to produce such constructs using conventional methods.

Another aspect of the present disclosure is the use of recombination functions from the bacteriophage λ in *E. coli*. The recombination function of λ phage is carried out by two gene products, exo, a nuclease that acts progressively on double strand DNA to generate a 3' single stranded overhang and beta, a single-strand DNA (ssDNA) binding protein capable of annealing complementary ssDNA strands. In certain preferred embodiments, the homologous recombination includes the inactivation of the *E. coli* RecBCD by a λ phage gam gene product.

In the screening assays, one may insert a linear DNA fragment composed of a selectable marker flanked by regions of homology to the gene of interest into a library containing cell culture by electroporation and subsequent selection for the drug resistance marker. In the second type of assay one may also provide the recombinogenic fragment in vivo by placing the fragment encoding the selectable marker flanked by regions of homology into a specialized plasmid designed so that the fragment can be excised in the cell by an inducible restriction enzyme. Growing a phage library on the cells that are excising the fragment allows for the recombination to occur and phage incorporating the selectable marker can then be selected. Utilizing this system, a positive selection marker may be flanked by regions of homology of only about 28–50 bases on each side, and recombined into a genomic library to screen for the gene of interest. The use of this efficient recombination function with a positive selection marker allows rapid library screening and isolation of clones without the time-consuming steps of plaque lift or PCR based assays.

Included in the present disclosure are also preferred methods of constructing a genomic library in a λ bacteriophage cloning vector system, in which the vector may contain a removable stuffer fragment that expresses a lambda repressor gene. In the use of this system, vectors will only form plaques if the stuffer has been replaced by a genomic DNA fragment, greatly simplifying genomic library construction. Another advantage of preferred cloning vectors is that the preferred vectors are automatically converted from a phage to a plasmid by utilizing a recombination system such as the cre-lox mediated recombination system.

In certain embodiments, the present invention may be described as a method of screening a DNA library for a gene of interest, including the steps of obtaining a DNA library containing the gene of interest, obtaining a nucleic acid fragment that encodes a bacterial positive selection marker flanked by DNA fragments that are homologous with respective sequences contained in the gene of interest and transforming a host cell containing the library with the nucleic acid fragment, where the host cell is an *E. coli* cell that expresses a highly efficient recombination function. As used herein the term transforming a cell is meant to convey its ordinary meaning as understood in the art. Transformation indicates that a gene has been introduced into a prokaryotic cell and is stably replicated in that cell. The most preferred cells express the exo and beta recombination functions of bacteriophage λ. It is an aspect of the disclosure that other bacterial cells with an enhanced recombination function could also be used to practice the disclosed methods. Particularly other enteric bacteria or other gram negative cells may be used for library screening. It is also understood that homologs of exo and beta derived from phage other than lambda may also be used in the methods of the present disclosure. In alternative embodiments, the endogenous bacterial recombination functions such as the RecE and RecT genes of *E. coli* and their homologs in other bacteria may be enhanced by overexpression in order to achieve library screening using homologous recombination.

In the practice of a preferred method, one incubates the host cell under conditions effective to allow the fragment to recombine into the library and the host cells are grown under selective conditions to identify recombination events. For example, if the selection marker is tetracycline resistance, then the cells would be incubated in media containing tetracycline so that only cells expressing the marker would survive. Colonies of selected cells can then be further tested to confirm which represent homologous recombination events and clones may be isolated from those colonies.

The methods and compositions of the present invention are applicable to any type of target DNA, including but not limited to genomic libraries, cDNA libraries, bacterial artificial chromosome (BAC), or cosmid libraries, and which may be derived from any organism or type of organism, such as an animal, bacteria, plant, or yeast. The DNA may be derived, therefore, from a mammalian, insect, plant, fish, mouse, rat, human, primate, bovine, ovine, feline, canine, porcine, guinea pig, rabbit, hamster, Drosophila, *Caenorhabditis elegans*, Arabidopsis, corn, wheat, rye, rice, or avian source, or from any other plant, animal, bacteria or yeast in which enough DNA sequence is known to create the targeting homology.

It is an aspect of the disclosure that in certain embodiments the bacteriophage λ exo, and beta recombination functions are expressed in the host cell. In addition, the λbacteriophage gam gene may be expressed in the host cell as well as the *E. coli* recA gene. One or more of these genes may be expressed from a plasmid in the host cell, or one or more of them may be integrated into the genome of the cell. The recombination genes may also be expressed from a constitutive promoter, however, more preferred is a regulated promoter. A regulated promoter is a promoter that only initiates DNA transcription when certain conditions are met in the cell. Such conditions include the presence or absence of a certain chemical, salt or metabolite, a certain temperature, the presence of phage anti-termination proteins or particular polymerases such as the T7 RNA polymerase. Certain regulated promoters include conditional or inducible promoters that are activated in the presence of a certain nutrient that may be a sugar such as lactose, galactose or arabinose or analogues thereof such as the araB, lacZ, galE or tac promoter. Other types of regulated promoters include the trp promoter, the λ PL or PR promoters or the tetracycline promoter.

The bacterial positive selectable marker to be recombined into the target DNA may be any marker known in the art, and is preferably an antibiotic resistance marker, and may also be a nutritional marker or a tRNA gene or a λ gene. Antibiotic resistance markers may include, but are not limited to resistance to ampicillin, tetracycline, streptomycin, penicillin, chloramphenicol or neomycin. In certain embodiments, a second bacterial marker is expressed on the library plasmid or vector. In this way, a double selection is possible so that both the resistance expressed in the targeting construct and the resistance expressed from the library vector must be present for a positive selection. In those embodiments in which the gene isolated from a library is to be used as a targeting vector, or as a vector in a eukaryotic cell, a eukaryotic positive selection marker may be placed adjacent the bacterial positive selectable marker in the targeting fragment to enable one to select homologous recombinants in a eukaryotic cell.

In certain embodiments, a linear fragment containing the targeting construct is introduced into a cell by electroporation or other means known in the art. In alternate embodiments, the fragment may be introduced as a plasmid, and the fragment removed by a restriction enzyme in vivo. In this second embodiment, the fragment is preferably flanked by restriction sites that are recognized by a restriction enzyme that is expressed by the host cell under the control of an inducible promoter such that the fragment can be controllably excised to allow homolgous recombination to occur. A preferred restriction enzyme for use in *E. coli* is I-SceI.

Although it is understood that one may practice the present invention using any pre-existing library that is available, one may also construct a library. A preferred vector for use in such aspects of the practice of the invention would include a lambda left arm segment, a recombination site, a multicloning site containing a plurality of restriction endonuclease recognition sequences, a stuffer fragment, wherein the stuffer fragment encodes a lambda gene under the control of a constitutive promoter, the expression of which affects the packaging or lysogenic growth of bacteriophage λ, a second multicloning site containing a plurality of restriction endonuclease recognition sequences, possibly a negative selection marker such as herpes virus thymidine kinase under the operative control of a promoter, effective to act as a negative selection in a eukaryotic host, a bacterial positive selection marker, a bacterial origin of replication, a direct repeat of the recombination site and a lambda right arm segment. A preferred library may be constructed by removing the stuffer fragment by endonuclease digestion, ligating the digested vector in the presence of fragments of DNA that encode the library sequences and amplifying the plaque forming units. In certain embodiments, the method would also include infecting an *E. coli* host cell wherein the host cell expresses a site specific recombinase gene product effective to convert the library to plasmid form. It is also understood that a lambda suppressing gene, such as the repressor cI may be expressed at high levels by the host cell, rather than from the vector and that such expression would also maintain the library in plasmid form.

A recombinase target site, or sequence specific recombinase target site is a short nucleic acid segment or sequence that is recognized by a sequence or site-specific recombinase and that becomes a crossover region during the site-specific recombination event. Preferred recombination sites include loxP, loxP2, loxP23, loxP3, loxP511, loxB, loxC2, loxL, loxR, loxΔ86, loxΔ117, frt, dif, RS or att. The lox sites are nucleotide sequences at which the product of the cre gene of bacteriophage P1, Cre recombinase, can catalyze a site-specific recombination event. The frt recombination site is a nucleotide sequence at which the product of the FLP gene of the yeast 2 µm plasmid, FLP recombinase can catalyze a specific recombination event.

In the preferred library vector, the stuffer fragment encodes the lambda cI gene under the control of a strong constitutive promoter. A strong constitutive promoter is desired so that the vector will not make plaques if the stuffer is intact, but will only form lytic plaques when the stuffer is replaced by target DNA. A preferred promoter is the Con I promoter. A strong constitutive promoter is defined herein as a promoter that requires no inducer and is sufficiently active to direct expression of an amount of repressor protein effective to block λ replication.

The invention may also be described in certain embodiments as a method of obtaining a targeting vector for use in producing a mammalian embryonic stem cell with a disrupted gene of interest. This vector is then effective for producing a knock out mammal. The preferred method includes obtaining a DNA library comprising said gene of interest of said mammal; obtaining a nucleic acid fragment that encodes a bacterial positive selection marker and a eukaryotic positive selection marker flanked by DNA fragments, wherein said DNA fragments are homologous with respective sequences contained in the gene of interest; co-transforming a host cell with the library and with the nucleic acid fragment, wherein the host cell is an *E. coli* cell that expresses the exo and beta recombination functions of bacteriophage λ; incubating the transformed host cell under conditions effective to allow homologous recombination between, the library and the fragment such that the selectable marker is transferred into the library vector; incubating the host cell in a selective medium to select recombination events; and isolating a clone from the selected cell.

The present invention also encompasses methods of screening a library for a selected nucleic acid sequence. The methods include inserting a selectable marker into the library at the position of the selected sequence by homologous recombination in an *E. coli* cell, wherein the *E. coli* cell expresses a bacteriophage λ recombination function, preferably the exo and beta recombination functions of bacteriophage λ.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1A:
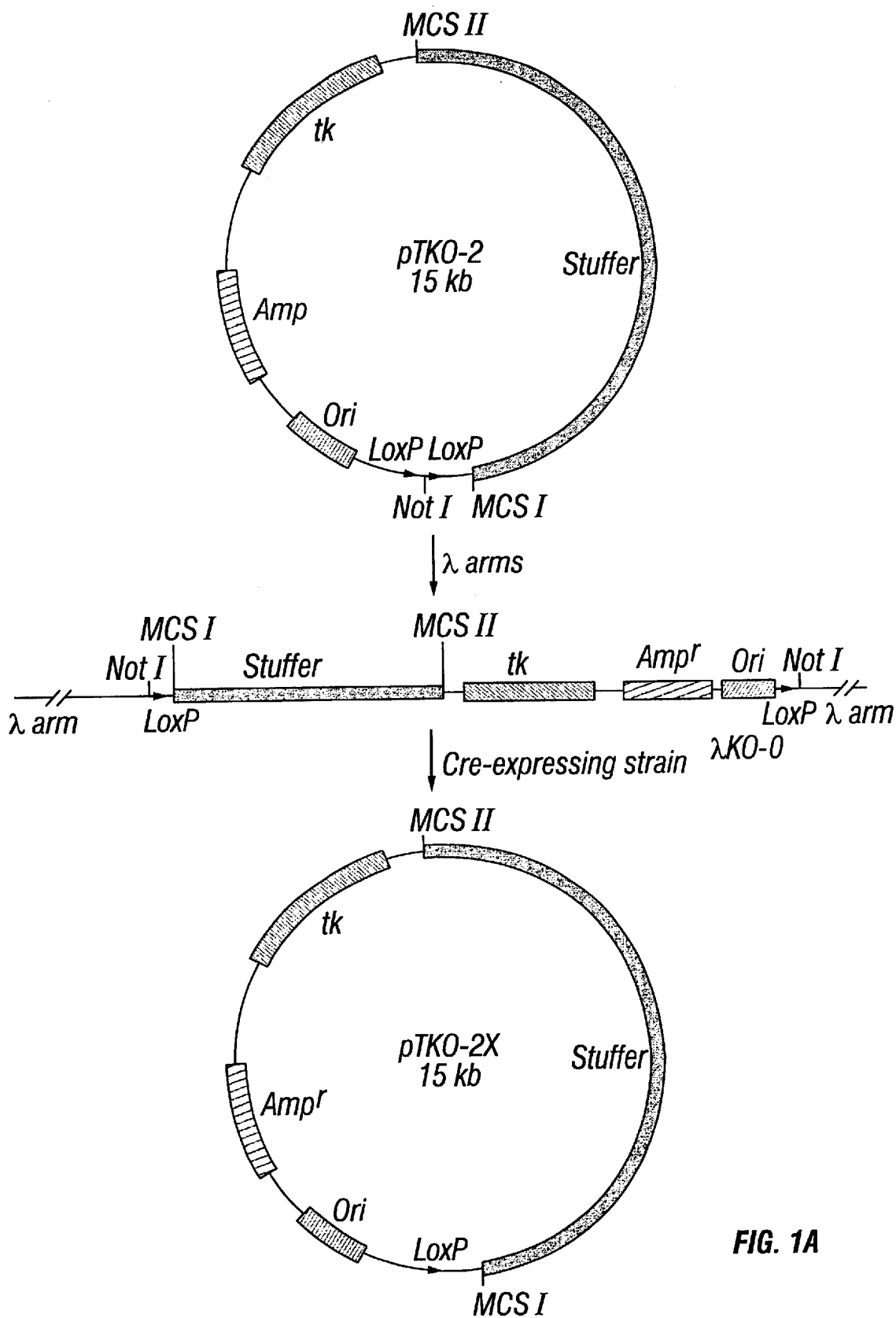
FIG. 1A is a schematic representation of the generation of λKO-0 and the Cre-mediated conversion from phage to plasmid.

The present disclosure provides compositions and methods that greatly improve and simplify conventional methods of identifying and manipulating genomic DNA, with particular application to the production of targeting vectors for replacement or inactivation of a selected gene in an animal such as a rodent. Typically, several hybridization events are required to isolate and identify a particular gene from a library, and this isolated clone is then used to generate a final gene replacement construct, which requires several subcloning events. The present invention eliminates many of these time consuming steps. In preferred embodiments, a positive eukaryotic selection marker such as PGK-NEO or HPRT is placed adjacent a bacterial selectable marker, preferably a tetracycline resistance gene or the neomycin phosphotransferase gene, nptA, from Tn903, that confers kanamycin resistance on E. coli. Although these are preferred selection markers, any known markers may be used in the practice of the invention as long as one gene is selectable in bacteria and the other is selectable in a mammalian cell. This dual gene cassette then has oligonucleotide sequences attached to it by ligation to produce a construct that has about 28, 29, 30, 40, 50 or even 70 or more base pairs of homology to the genomic DNA flanking the region one wishes to replace. The number of base pairs of homology is chosen for the convenience of the practitioner and may include as much sequence as is needed, including an entire gene or an entire exon or other coding region in some cases. However, there are clear advantages to being able to perform homologous recombination with small regions of homologous sequence that can be easily synthesized chemically. The present invention allows the use of segments of homology as low as about 29 bases on each side of the markers.

In preferred methods of practicing the invention, an E. coli cell with the target library and that expresses lambda recombination functions as described herein, may be transformed with an isolated fragment containing the dual markers flanked by homologous regions (the adapter-cassette fragment). In other embodiments, the linear adapter-cassette fragment may be provided to the cell in a plasmid and produced in vivo by an inducible restriction enzyme. In the practice of this embodiment, then, one simply provides the induction signal to the cell, and the restriction enzyme is expressed and removes the recombinogenic fragment from the plasmid. Homologous recombination then occurs as in the embodiments in which the fragment is supplied directly through electroporation for example.

Typically, the plasmid containing the library also expresses one or more antibiotic resistance markers so that recombination events can be selected based on dual antibiotic resistance. For example, when the adapter-cassette contains a kanamycin resistance marker and the library plasmid contains an ampicillin resistance gene, the selection would include growing the transformed cells in the presence of both antibiotics. Cell growth under such conditions would indicate that the adapter-cassette had replaced the target region of DNA. Thus, the marker fragment both identifies the correct clone from the library and allows the isolation of the clone based on antibiotic selection in a single step. The present inventors have demonstrated the success of the described system by insertions as well as by replacing genetic regions of up to 2.8 kB via homologous recombination.

Although any DNA source may be used as the target DNA, including libraries that are currently available commercially, and including cDNA or genomic libraries, for example, in certain embodiments one may wish to construct a library to be screened by the methods described herein. In those embodiments, certain k phage vectors are preferred for constructing genomic libraries. For example, preferred vectors have a region of the λ DNA replaced by a stuffer fragment that contains a constitutively expressed gene that affects the packaging or lysogenic growth of the phage. The preferred stuffer fragment contains a lambda cI repressor under the control of a strong constitutive promoter such as the Con I promoter. The expression of cI prevents the phage containing this stuffer from replicating as a lytic phage, and it is propagated as a plasmid lysogen in E. coli. A strong constitutive promoter is preferred to ensure that only those phage that have the stuffer replaced with a DNA insert from the library are able to replicate as plaque forming units. The stuffer fragment can be removed by digestion with a restriction enzyme, preferably BamHI, which allows DNA of from about 15 to about 19 kilobases (kB) in size to be inserted as MboI or Sau3AI partial digestion fragments, or as BamHI, BglII or BclI fragments. After packaging, only phage that have replaced the stuffer fragment with genomic DNA can form plaques, providing a selection for inserts (FIG. 1D). In addition, by putting the cI gene into an *E. coli* chromosome, *E. coli* strains have been generated that support the lysogenic replication of λ phage that carry a plasmid origin of replication and appropriate drug markers. Another feature of the preferred vectors is that the λ vectors contain a plasmid that can be excised by cre-lox mediated recombination in *E. coli*. The genomic or target DNA inserts reside within the plasmid region of the lambda vectors and become part of the plasmid after excision by cre-lox mediated recombination. This facilitates conversion of the library from phage to the more stable plasmid form without having to resort to removing the inserts with restriction digestion and subcloning into a plasmid. These preferred vectors are also designed to simplify construction of gene targeting constructs, by including a gene encoding the viral thymidine kinase (TK) under the control of the MC1 promoter adjacent to the cloning site within the plasmid portion of the vector. TK can be selected against by the presence of gangcyclovir and is useful as a negative selection marker against random recombination and to enrich for homologous recombination events in mammalian cells. Thus, the tk marker is adjacent to each DNA insert in the plasmid vector after the cre-lox mediated recombination. In addition to the features discussed, the preferred vectors contain a number of rare restriction sites effective for linearizing the finished knock out (KO) constructs before electroporating them into ES cells. In certain embodiments, the restriction sites are recognized by an inducible restriction enzyme such as the I-SceI enzyme that may be used to excise the recombinable fragment from a plasmid in vivo. The final step for generation of a knockout construct is the replacement of exon sequences from the target gene with a selectable marker, allowing the positive selection of homologous recombination events.

After the library is constructed, the present disclosure provides an improved method of isolating the gene of interest and constructing a targeting construct for creating a knock out mouse, for creating a site directed mutation in a gene of interest, or for engineering of large DNA clones such as a bacterial artificial chromosome (BAC), for example. As part of the present disclosure, homologous recombination in *E. coli* is used to precisely replace selected exon sequences with markers needed for selection of subsequent homologous recombination events in mammalian cells. This circumvents the need to generate constructs by conventional cut and paste methods. In addition, by utilizing λ phage encoded recombination functions, homologous recombination efficiency in an *E. coli* host is shown to be high enough for library screening, with as little as 58–100 bp total homology.

The following methods were used in the studies described in the following examples and are provided herein as examples of preferred modes of practicing the methods disclosed herein.

Construction of λKO phage vectors and genomic libraries. λKO-0 is a phasmid replacement vector (Elledge and Walker, 1985) designed to facilitate genomic library construction for the purpose of making gene knockouts in ES cells. λKO-0 contains the thymidine kinase (TK) gene driven by the pMC1 promoter placed directly adjacent to the site of genomic DNA insertion (FIG. 1A). The TK gene is used in a positive-negative selection scheme used to make gene knockouts in ES cells, however, selection against TK is not required for homologous recombination in ES cells. It is also understood that any negative selection marker may be used, or a color marker may be used, for example. Examples of other markers that may be used include, but are not limited to green fluorescent protein (GFP), luciferase or lacZ, for example. λKO-0 also has cre-lox automatic subcloning capability as developed by the present inventors for the λYES system (Elledge et al, 1991), obviating the need for purification of lambda DNA and subsequent subcloning of inserts.

To generate λKO-0, a plasmid vector, pTKO-2 (FIG. 1A), was constructed that contains a ColEl origin of replication from pBR322, the bla gene for replication and selection in *E. coli*, pMCl-TK for negative selection in mammalian cells, a stuffer fragment of 10 kB, and direct repeats of loxP sites flanking a Not I restriction site. pTKO-2 was linearized by Not I digestion, ligated to λ arms derived from λFIX II, and packaged in vitro to generate λKO-0 (FIG. 1A). λKO-0 is readily converted to aplasmid by infecting a Cre-expressing strain such as BNN132, (Elledge et al., 1991) (FIG. 1A). To use λKO-0 as a phage vector, the stuffer is removed by BamH I digestion followed by gel purification of the lambda arms. λKO-0 arms can accept inserts generated by BamH I, Bgl II, Mbo I, or Sau3A I digestion, with sizes from 4 to 18 kB. Inserts are flanked by a host of restriction sites including several rare cutters to facilitate linearization for electroporation into ES cells.

Figure 1B:
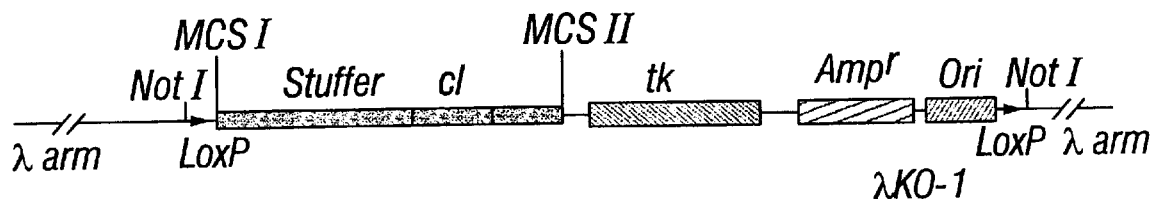
FIG. 1B is a schematic diagram of the phage vector λKO-1.
Figure 1C:
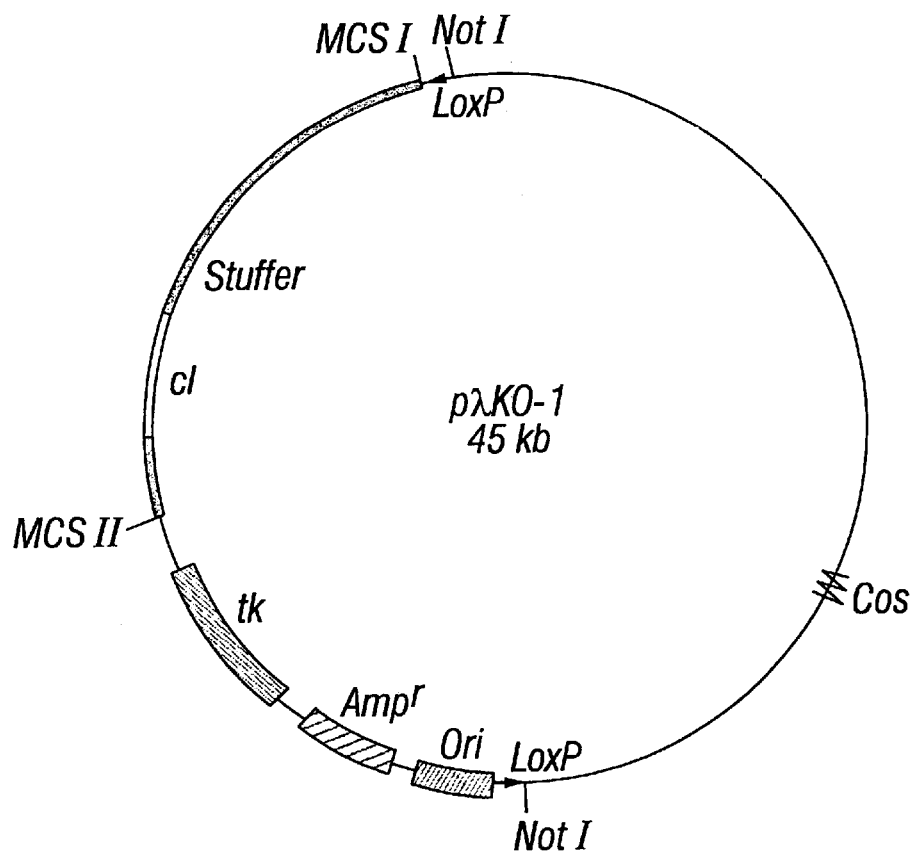
FIG. 1C is a schematic diagram of the linear and plasmid forms of pλKO-1.
Figure 1D:
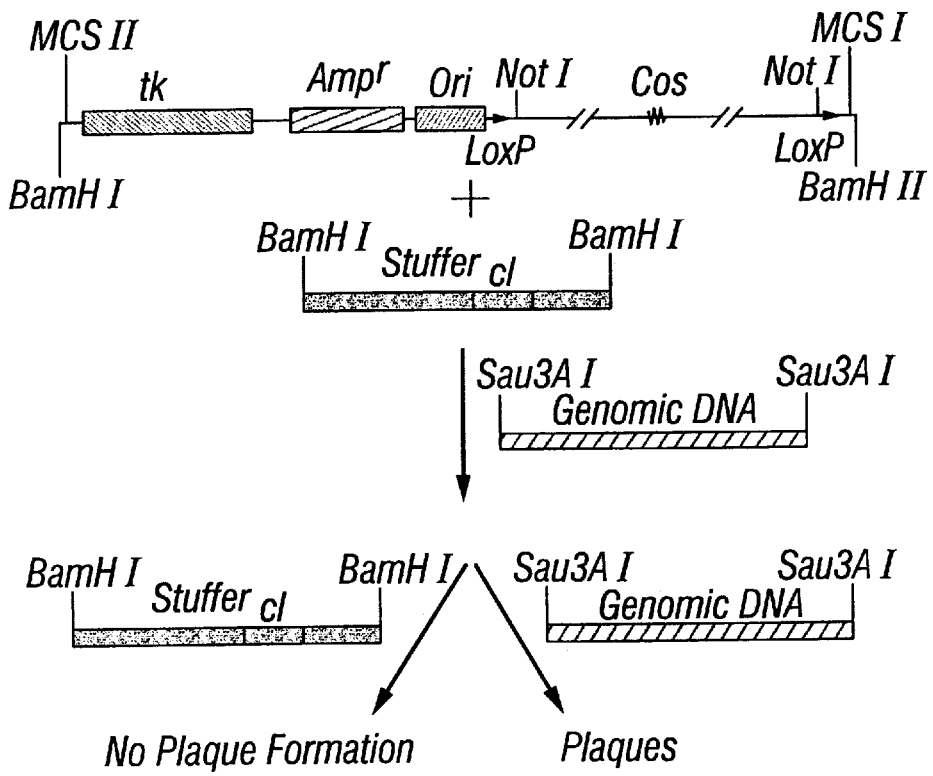
FIG. 1D is an example of a method of using λKO-1 for a genomic library construction.
Figure 1E:
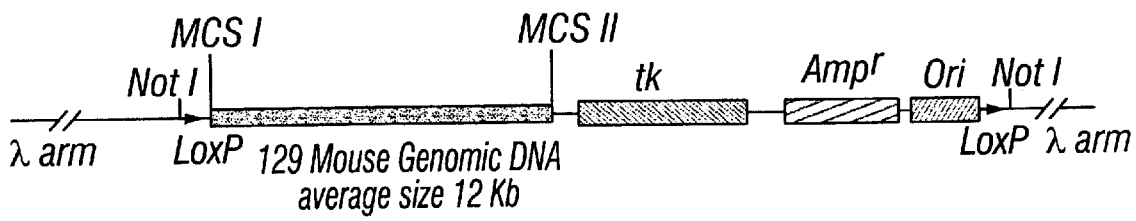
FIG. 1E is a schematic diagram of the 129 mouse genomic library.

To further facilitate genomic library construction, a genetic selection for inserts into λKO-0 was developed. Previous selections of this sort were based on the spi$^+$ selection scheme in which the lambda red gam genes were present on the replacement stuffer fragment. Phage containing this stuffer are unable to make plaques on *E. coli* cells containing a lysogenic P2 phage. While the spi$^+$ selection successfully selects for genomic insert bearing phage, lambda grows very inefficiently on P2 lysogens and the effects of P2 encoded function on the stability of complex genomic DNA are unknown. To circumvent these issues, a new selection was developed by including cI, the gene encoding the lambda repressor on the stuffer fragment, under the control of a strong constitutive promoter, ConI (Elledge and Davis, 1989). cI is capable of repressing the transcription of lambda phage genes, forcing lysogenization of phage in which its expression persists. By replacing the stuffer in λKO-0 with the ConI-cI containing stuffer, λKO-1 was generated (FIG. 1B). λKO-1 cannot form plaques due to the high level expression of cI, but it can lysogenize *E. coli* and grow as an Ap-resistant plasmid (FIG. 1C) which facilitates its purification by CsC1 gradient centrifugation methods. In the preparation of genomic libraries using λKO-1, only phage containing genomic inserts can form plaques, establishing the selection for inserts and circumventing the need for purification of lambda arms (FIG. 1D). In a test, λKO-1 was digested with BamHI and ligated with and without an insert. The insert to vector molar ratio was 2:1. Both ligations were packaged in vitro. The vector with insert DNA exhibited greater than 200-fold stimulation in plaque forming units (pfu).

λKO-1 was then used to construct a mouse genomic library. λKO-1 was purified as a plasmid lysogen (pλKO-1). Mouse strain 129 genomic DNA was digested with Sau3A I and 10–14 k DNA fragments were obtained by centrifugation through a sucrose gradient. For library construction, pλKO-1 was prepared by BamH I digestion and ligated to size fractionated genomic DNA fragments in a 2:1 insert to vector ratio, followed by in vitro packaging. A library was obtained with enough plaque forming units to include inserts totaling 50 times the size of the mouse genome. This library was amplified once. A diagram of the library is illustrated in FIG. 1E. Genomic inserts in λKO-1 were examined by infection of library phage into cre-expressing BNN132. Restriction analysis of the AP$^R$ colonies revealed that 40 out of 40 clones contained inserts with an average size of 12 kB.

Several genes were isolated from this library through the conventional plaque lifting method. These genes were isolated at expected frequencies. Southern blotting analysis indicated no rearrangements in these clones in comparison to genomic DNA.

Preparation of linear DNA fragments used in homologous recombination. Two linkers are generated by annealing a long (50–70 nt) and a short (20 nt) oligonucleotide fragment. The short one is phosphorylated at the 5' end which also has a 4-base overhang after annealing. The 4-base overhang (different in each linker) is compatible with the sites used to cut selection markers. The linkers are ligated with gel purified DNA fragments containing a selection marker at a molar ratio of 10:1 in order to suppress marker DNA self ligation. The ligation is incubated one hour at room temperature. The linker flanked selection marker DNA is gel purified, ends flushed with Klenow DNA polymerase and used in electroporation without further purification.

To generate DNA fragments for electroporation using the PCR, primers are synthesized that contain 50 bases used for homologous recombination and 20 bases for annealing to a selection marker. A 50 µl reaction consists of 5 µl 10× reaction buffer (Fisher Biotech), 3 µl 2.5 mM MgCl, 1 µmM 2.5 mM dNTP, 1 µl each of the primers at 10 µM, 0.5 µl Taq polymerase (Fisher Biotech), 1 ng template DNA, and water. Cycle conditions are 1) 94° C., 3 min; 2) 94° C., 15 sec; 3) 55° C., 30 sec; 4)72° C., 1 min; 5) cycle back to step 2 for 35 times; 6)72° C., 10 min; 7) stay at 4° C.; 8) end. PCR products are gel purified.

Preparation of Competent Cells and Electroporation

Bacterial cells are grown in LB media containing half the salt until the optical density (OD) reaches 0.4. Cells are chilled in ice for 10 min and centrifuged. Cell pellets are washed twice with cold 20% glycerol and suspended in 20% glycerol at a density of $5 \times 10^9$/ml (1 OD equals approximately $8 \times 10^8$ cells). Cells are used either immediately or frozen in liquid nitrogen and stored at −80° C. Freezing of competent cells typically decreases electroporation efficiency by a factor of 2 to 4. DNA is electroporated into cells using a Gene Pulser II (BioRad) set at 2.5 kv and 200 ohms resistance. Immediately after electroporation, cells are transferred into warm LB and recovered at 37° C. for 1 hour before being spread on plates.

Generating KO Constructs and Screening Libraries via Homologous Recombination in E. coli To generate gene targeting constructs, 1 µg of homology flanked DNA fragments containing PGK-neo and Kan$^r$ is electroporated into 40 µl electro-competent JC8679 cells along with 1 µg of plasmid DNA containing the gene of interest. The cells are spread on plates containing ampicillin and kanamycin. A small fraction ($\frac{1}{10^6}$) is spread on a plate containing ampicillin only for the purpose of monitoring electroporation efficiency.

Figure 3A:
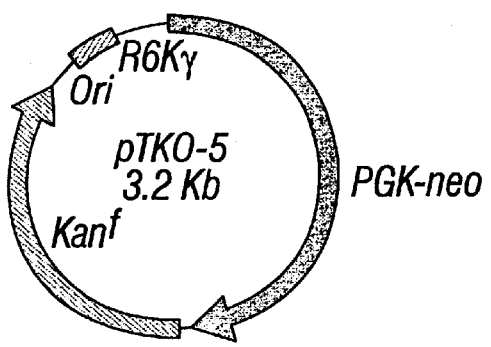
FIG. 3A is a schematic diagram of pTKO-5, described herein as used in the production of gene targeting constructs without subcloning.

To screen a library with homologous recombination by transformation of homologous DNA, a bacteria strain, SCRN3 was constructed in two steps. The plasmid pML104 (FIG. 3C) was introduced into DH10B cells (Life Technology). The resulting strain was infected with a λ phage carrying a cre-expression cassette and chloramphenicol resistant gene. A phage lysogen was selected by selecting for chloramphenicol resistance. SCRN3 is grown at 30° C. in LB containing spectinomycin to an OD of 2. From the culture, $2 \times 10^{10}$ cells are incubated with an equal number of library containing phage for 30 min at 30° C. with agitation. Phage infected cells are transferred to 500 ml fresh low salt LB containing ampicillin (50 µg/ml), spectinomycin (25 µg/ml) and IPTG (0.4 mM), and grown for 2 hrs at 30° C., at which time the OD is 0.4. Cells are harvested and processed for use in electroporation. Under the same conditions, if the phage is omitted, no growth of the cells is observed, and the cells undergo lysis due to the presence of ampicillin.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Subcloning by Gene Replacement in E. coli

Figure 3B:
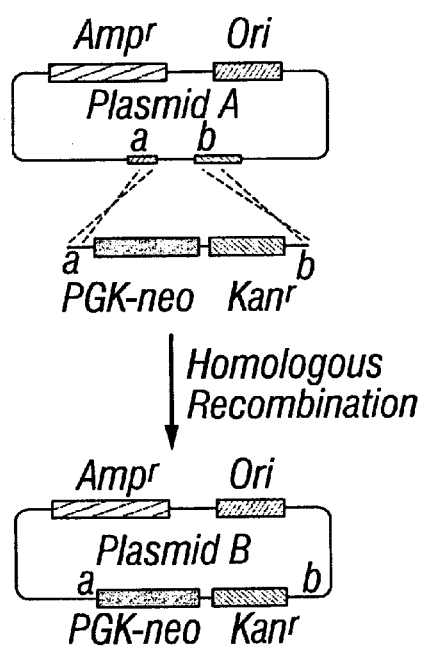
FIG. 3B is a schematic diagram of gene replacement in *E. coli* via homologous recombination, in which crossover via homology (represented by a and b) is depicted by the dashed lines. Only the recombinants (Plasmid B) can confer both ampicillin and kanamycin resistance.
Figure 3C:
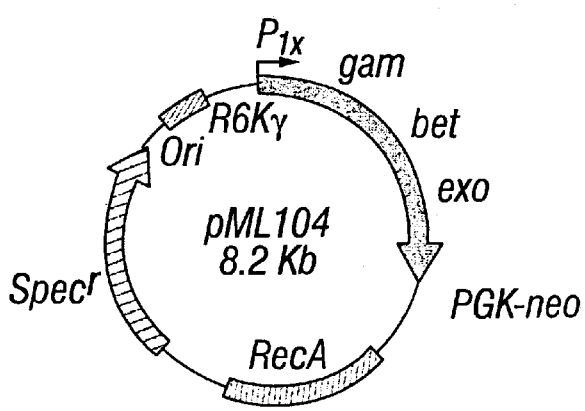
FIG. 3C is a schematic diagram of pML104 carrying λ phage recombination genes. This plasmid is shown herein to render *E. coli* strains proficient in homologous recombination.

It has previously been shown that JC8679, the E. coli strain mutant for the recombination genes RecBC can take up linear DNA and recombine it to its chromosome or resident plasmids via homologous regions on the introduced linear DNA (Winans et al., 1985). A plasmid, PTKO-5 (FIG. 3A), was constructed containing PGK-neo for selection in mammalian cells and Kn$^r$ for selection in E. coli. The PGK-neo/Kn$^r$ fragment is excised with two different restriction enzymes and ligated at each end with double stranded oligonucleotides containing 50 to 70 base pairs of homology to sequences flanking the region to be replaced in the gene of interest (FIG. 3B). The resulting DNA fragment is electroporated into JC8679 simultaneously with the target plasmid (Plasmid A). E. coli transformants are selected on LB plates containing both ampicillin and kanomycin. Since Kn$^r$ colonies can arise from transformation of even a small trace of the original PGK-neo/Kn vector, the R6Kλ origin of replication was used. This is a conditional origin of replication dependent on the presence of the pir gene for replication. Since the pir gene is not present in JC8679 cells, only recombinants bearing the Kn$^R$ cassette (Plasmid B) survive the selection (FIG. 3B). The mouse p57KIP2 gene was chosen to test the efficacy of this recombination method. Under the conditions used, a homologous recombination frequency of $1 \times 10^{-6}$ (or one Ap$^R$Kn$^R$ recombinant per $10^6$ AP$^R$ resistant transformants) was achieved. No significant difference in recombination frequency was observed if the host plasmid (plasmid A) resided in JC8679 prior to electroporation of the linear DNA. All of the Ap$^R$Kn$^R$ resistant colonies examined had undergone homologous recombination as verified by restriction digestion. The inventors have also successfully targeted a gene of interest in ES cells using genomic clones isolated from the library and constructs made with methods described herein.

EXAMPLE 2

In order to achieve increased recombination efficiency a plasmid was constructed, pML104 (FIG. 3C), that carries the lambda exo, beta and gam recombination functions of bacteriophage λ as well as recA, designed to render any E. coli strain recombination proficient. It has been shown that recombination functions encoded by bacteriophage λ can promote homologous recombination in E. coli (Yokochi T, Kusano K, Kobayashi I, 1995, Genetics 139(1):5–17; Poteete AR, Fenton AC, Murphy KC, 1999, J Bacteriol 181(17):5402–8). In the plasmid, exo, beta and gam are under the control of the lac promoter inducible by IPTG, or other inducible promoter known in the art, making it possible to turn recombination functions on and off. pML104 is a Sp$^R$ derivative of pSC101 that has a temperature-sensitive origin that fails to replicate at 42° C. In IPTG treated cells containing pML104, homologous recombination frequencies of 1×10$^{10-}$(one recombinant per 10$^4$ transformants) have been achieved, a 100-fold increase over JC8976 cells. In various studies, pML104 has been used in *E. coli* strains XL1 Blue, BNN132 and DH10B with similar recombination frequencies, but with varying efficiency due to difference in electroporation efficiencies, with DH10B being the most transformable.

Library Screening via Homologous Recombination

To demonstrate screening the genomic library by homologous recombination, *E. coli* strain SCRN3 was constructed, which is *E. coli* DH10B containing plasmid pML104 and a lysogenized λCC (Cm$^R$, expressing cre). SCRN3 cells are incubated with mouse genomic library phage for 30 minutes for phage absorption, conversion to the plasmid form, and expression of Amp resistance. Infected cells are then grown in LB media containing ampicillin/spectinomycin to select cells that have absorbed phages and converted them to plasmids from which the bla gene is expressed. The lacZ promoter inducer, IPTG is added and the cells are incubated for 2 hours to allow IPTG to induce λ recombination gene expression from the plasmid pML104. The cells are made electro-competent and DNA fragments carrying a bacterial selection marker flanked by homology are introduced into these cells via electroporation. Homologous recombinants are selected on drug containing plates.

SCRN3 cells were found to give rise spontaneously to a substantial number of kanamycin resistant colonies without transformation. Therefore, to eliminate background, the selection marker was changed from Kn$^r$ to Th$^r$. SCRN3 does not produce Tcr background colonies. To examine recombination onto the library vector itself, a plasmid was constructed, pTK0-29, containing tet flanked by 50 bp sequences homologous to the tk gene present in λKO-1 from which the library is constructed. TK is present on every library phage and therefore serves as a control to measure the recombination frequency of this method. The tk/tet fragment was excised from the plasmid, gel purified, and electroporated into SCRN3 cells into which the mouse genomic library had been infected. There was a linear relationship between the number of recombinants and the amount of DNA fragment electroporated for reactions that contained up to 5 μg of DNA in 40 μl. The efficiency was 2×10$^5$ Tc$^R$ homologous recombinants per μg DNA. At this efficiency, there is expected to be 4 recombinants per electroporation with 40 Tc$^R$ with 40 μl competent cells and 5 μg DNA. This efficiency is sufficient for library screening via homologous recombination.

Figure 4A:
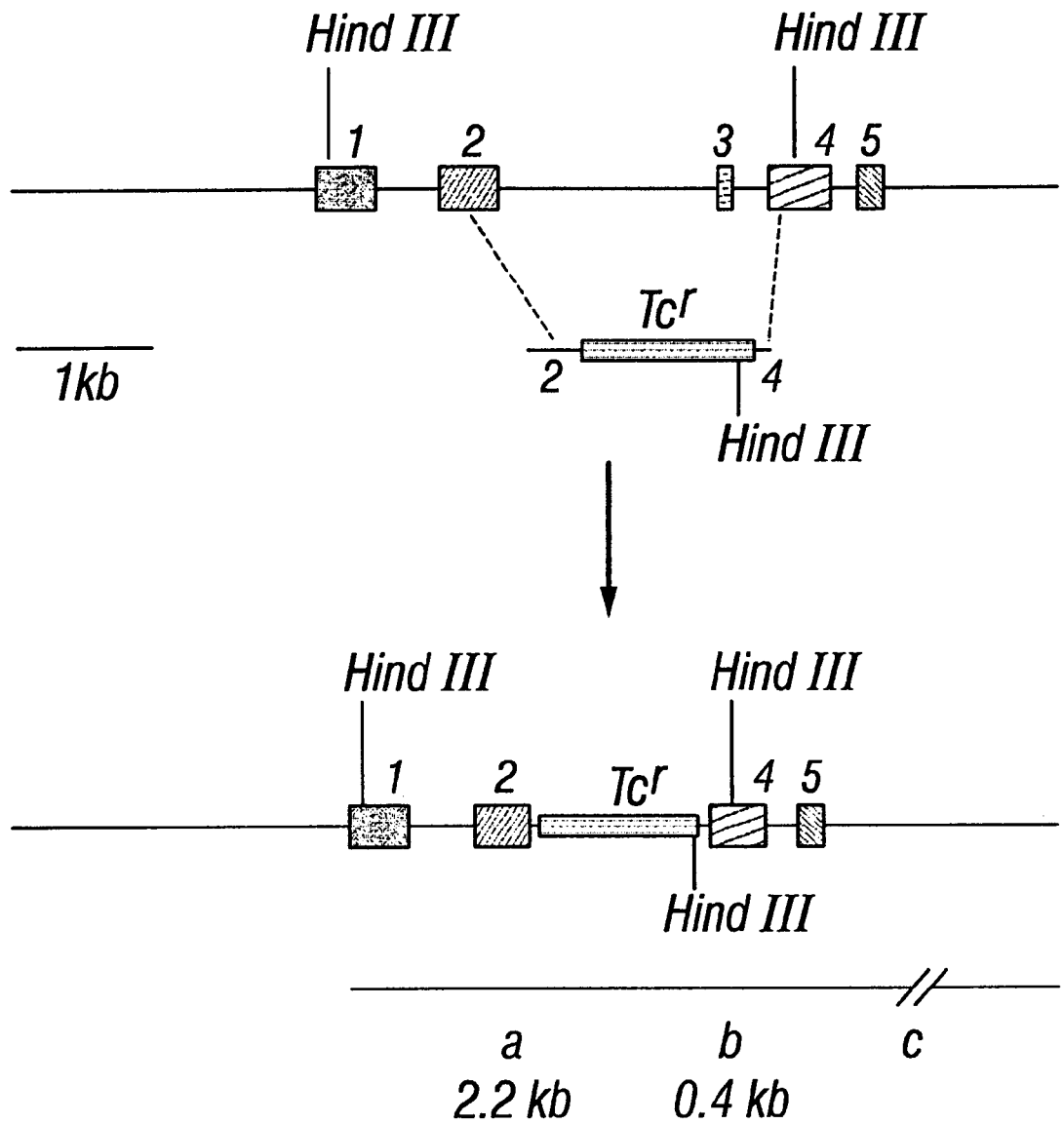
FIG. 4A is a schematic diagram of the genomic structure of the mouse PTTG gene including 5 exons, and the targeting fragment for screening as described as a preferred embodiment herein. The diagram illustrates three Hind III fragments (a–c), predicted to result from homologous recombination. Each fragment contains exon sequences and is able to be detected by Southern blotting with a cDNA probe.

The PTTG (pituitary tumor transforming gene) was chosen to demonstrate gene selection from the mouse library and simultaneous insertion of a selectable marker using homologous recombination. The PTTG gene was previously isolated from the library through conventional methods and its intron/exon structure had been characterized (FIG. 4). A plasmid construct was made in which the tet gene was flanked on each side by 76 bp homologous to sequence in exon 3 and exon 4, respectively. The plasmid was designated as pTKO-33. The PTTG/Tcr fragment was excised from the plasmid, its ends flushed, and the fragment was then purified by gel electrophoresis. Ten micrograms of the PTTG/TCR fragment and 80 μl of competent cells were used in a single electroporation. Nine Ap$^R$Tc$^R$ double resistant colonies were obtained, in agreement with the expected recombination frequency. Restriction digestion and Southern-blotting analysis of these clones indicated that all were derived from the mouse PTTG gene. All 9 clones contained a 0.4 kB Hind III fragment as predicted (FIG. 4), and the 9 clones were shown to be divisible into 6 overlapping groups (a–f) based on restriction mapping.

While the electroporation of the selectable marker flanked by homology into strains bearing the genomic library in plasmid form allows one to screen the library using homologous recombination, it has several features that could bear improvement. First, it requires a substantial amount of fragment, 5 to 10 micrograms. Secondly, the library needed to be made competent soon after conversion to its plasmid form in order to achieve optimal recombination frequencies. This limits the amount of competent cells one can generate from a given aliquot of library and consumes large amounts of library per electroporation. Third, the frequency of recombination allows the isolation of only a dozen or so recombinants per transformation and a higher number of recombinants would provide a more robust method.

Figure 2A:
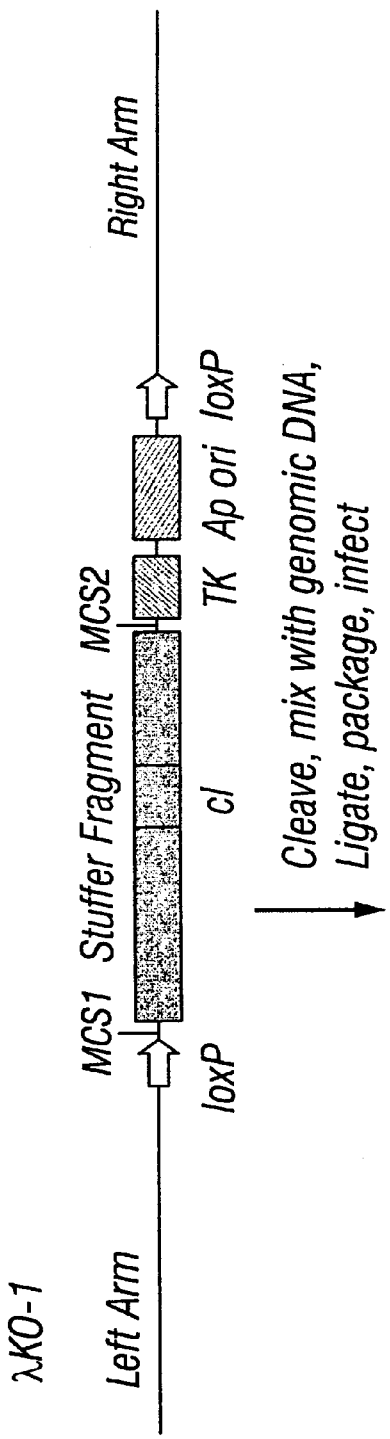
FIG. 2A is a schematic diagram λKO-1, a phage vector with the plaque repressor cI expressed from the stuffer fragment.
Figure 2B:
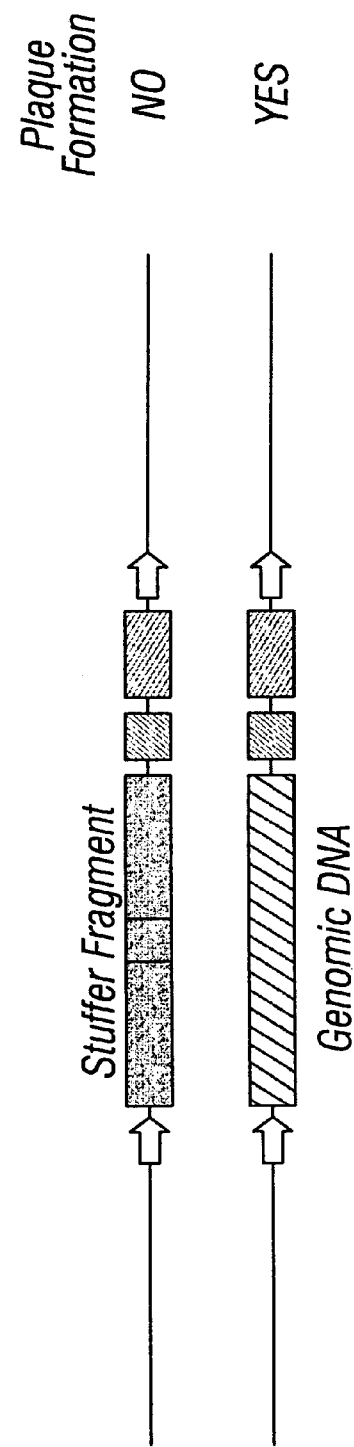
FIG. 2B demonstrates the selection based on the cI repressor in which only those vectors with genomic DNA replacing the stuffer are able to from plaques.
Figure 2C:
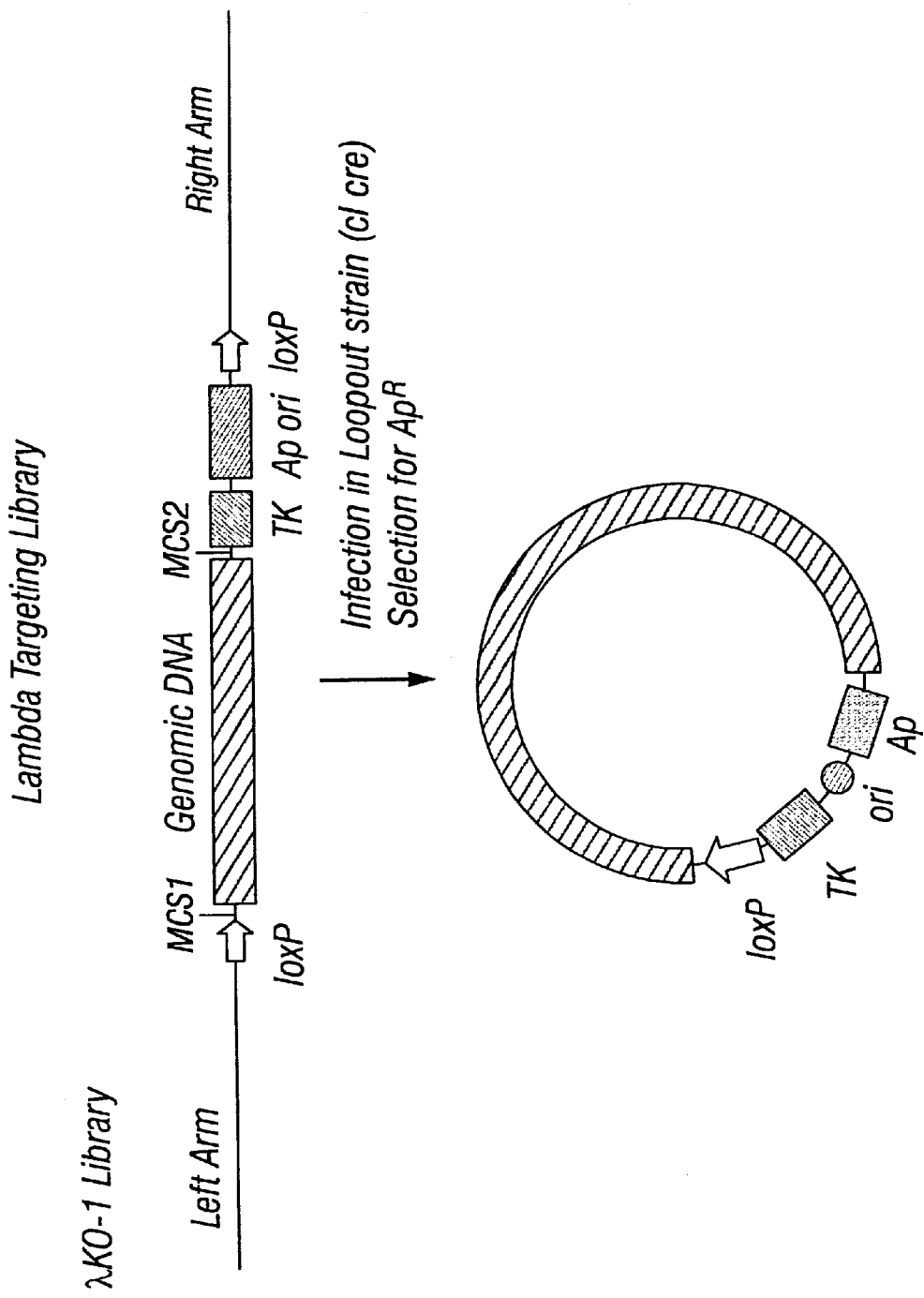
FIG. 2C is a schematic representation of the conversion of the phage library to a plasmid form by infection in a cre expressing strain.

To circumvent these drawbacks a second method was developed for achieving homologous recombination without the use of electrocompetent cells. Tis method included creating in vivo the same recombinogenic fragment that was previously created in vitro to target recombination. In brief, this method generates the recombinogenic linear fragment by induction of a restriction enzyme in *E. coli* that excises the recombination substrate from a resident plasmid. During the excision of this fragment, the λKO1 genomic library (FIGS. 2A–C) is allowed to replicate on the strain, thereby allowing the excised fragment to recombine with phage containing homologous DNA. The recombinants are recovered by converting the phage to plasmid DNA by infection into BNN132 or other suitable bacteria expressing cI and cre and selecting for the drug resistance marker that is recombined onto the phage (FIG. 2C).

Figure 5:
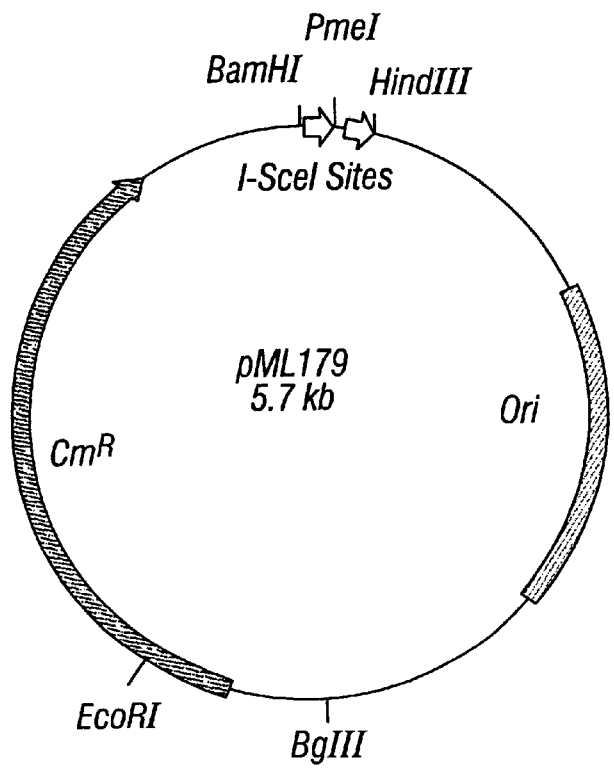
FIG. 5 is a schematic diagram of plasmid pML179 used to make constructs in which the recombinogenic fragment is excised in vivo.
Figure 6:
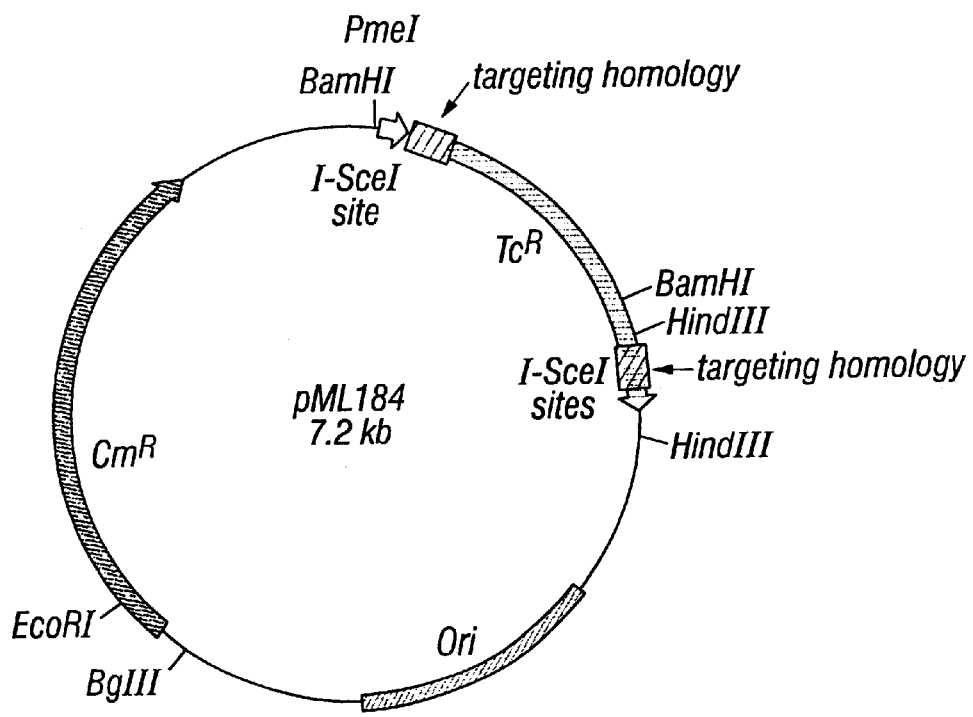
FIG. 6 is a schematic diagram of plasmid pML184 in which an adapter-cassette including a positive selection marker flanked by targeting homology to the gene of interest has been placed between the unique I-SceI restriction enzyme sites for excision of the cassette in vivo.
Figure 7:
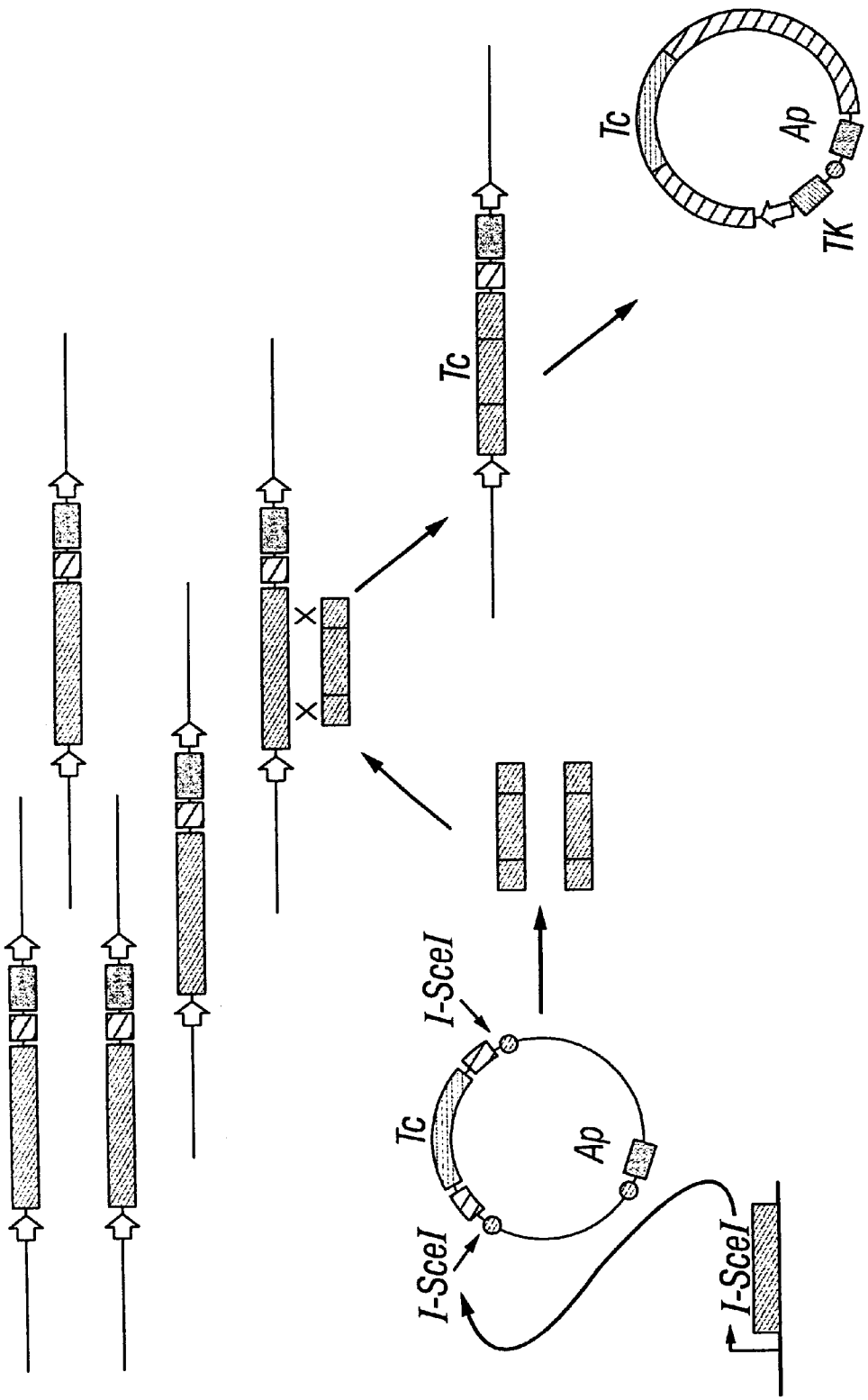
FIG. 7 is a schematic diagram illustrating in vivo recombination selection.

To accomplish this, the restriction enzyme I-SceI was employed. This enzyme recognizes an extremely rare 26 bp restriction site that is not present in mammalian genomes. A blunt fragment containing the TC$^R$ selectable marker flanked by 75 bp of homology to the PTTG gene was cloned into the PmeI site of pML179 (FIG. 5) to create pML184 (FIG. 6). pML179 is a Cm$^R$ high copy number plasmid derived from pDPT270 that was engineered to contain a PmeI site directly flanked by I-SceI sites (FIG. 5). pDPT270 is unrelated to pBR322 such that no homology is shared between λKO1 and any of the pML derivatives. pML184 was then introduced into SCRN10, which contains the recombination enhancing plasmid pML104 and the I-SceI gene under the control of the araBAD promoter integrated into the *E. coli* genome. To determine whether this strain could provide a sufficiently high recombination efficiency to make library screening feasible, its ability to transfer the Tc$^R$ marker to a phage that contained the genomic sequences for the PTTG gene, λKO1-PTTG was tested (FIG. 7). 1×10$^8$λKO-1-PTTG PFUs (plaque forming units) were infected into 1×10$^{10}$ SCRN10(pML184) cells and plated on 150 mm LB plates containing 0.002% arabinose to induce the I-SceI gene and 0.4 mM IPTG to induce the lambda recombination functions. The library was allowed to amplify for 8–10 hrs at 37° C. The resulting amplified phage, 1×10$^{11}$ total phage, were harvested and used to infect BNN132 selecting for Ap$^R$Tc$^R$. Ap$^R$Tc$^R$ colonies were observed at a frequency of 3×10$^{-5}$ Ap$^R$ colonies, or about 1 recombinant for every 75,000 homologous phage. Similar experiments using single burst infections of SCRN10/pML184 cells in liquid gave a recombination frequency of 5×10$^{-5}$ AP$^R$ colonies, or about 1 recombinant for every 20,000 homologous phage. No Tc$^R$ cells were isolated by amplifying this phage on similar cells lacking the I-SceI gene. Furthermore, of 24 Ap$^R$Tc$^R$ colonies, all had the restriction map predicted for homologous recombinants. Based on the estimate that $2\times10^5$ library phage cover the entire genome once given the insert sizes in the λKO-1 library, then one should be able to isolate homologous clones at a frequency of 1 in $4\times10^9$ library phage amplified on SCRN10(pML184) cells. Thus, isolation of homologous recombinants from a genomic lambda library via this genetic method is feasible and one would expect between 10 and 25 recombinants from $1\times10^{11}$ phage.

Figure 4B:
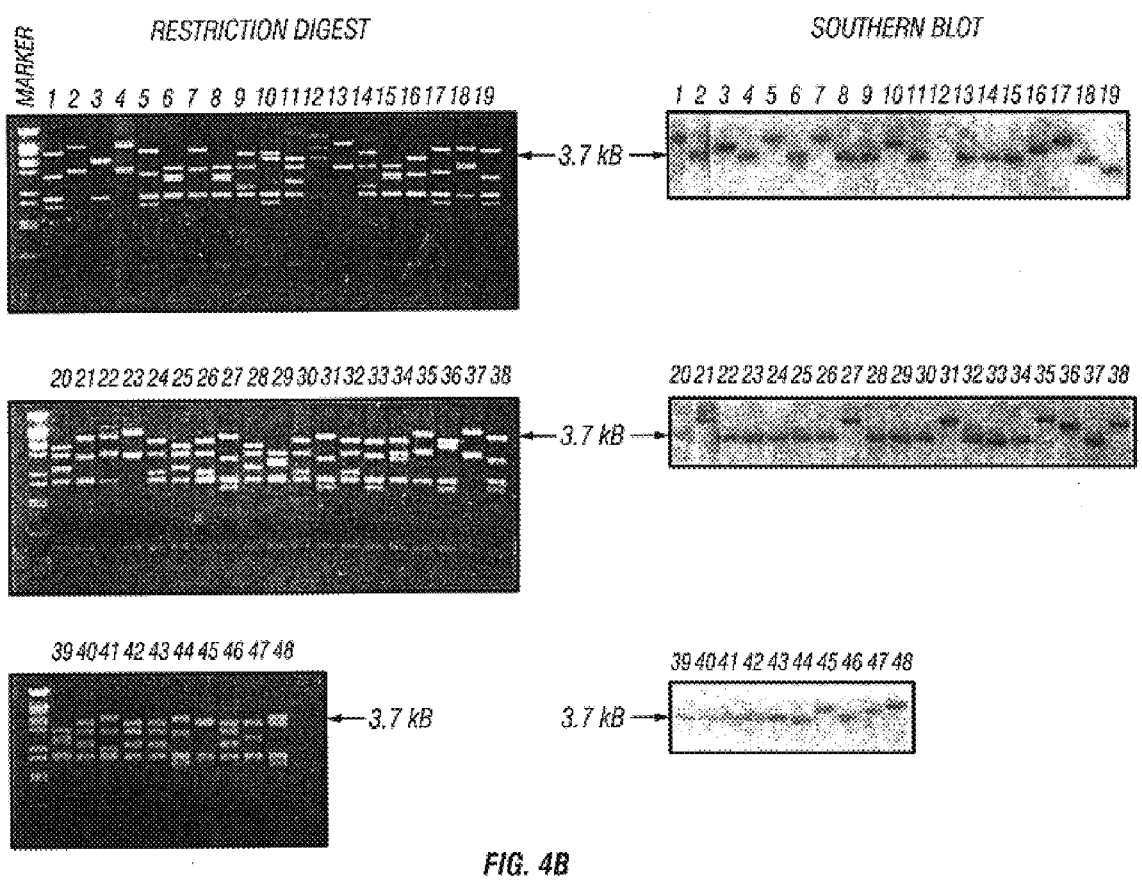
FIG. 4B is data from a library screening event in which a phage genomic λKO-1 library were infected into SCRN10 (pML184) cells in which the targeting fragment is excised in vivo by an inducible restriction enzyme. The library was amplified and $1 \times 11^{11}$ phage were recovered from the amplified library. These phage were then infected into an equal number of BNN132 cells for automatic subcloning. From these phage 300 $Ap^R Tc^R$ colonies were recovered and 48 clones were analyzed. The results of restriction digest of the 48 analyzed clones are shown. Forty seven of forty eight of these clones shared restriction fragments and represented 12 distinct genomic clones containing the target sequence. Also shown in the figure is the result of a Southern blotting analysis in which 47 of these 48 clones hybridize with a probe to the 3.7 kB HindIII fragment containing exon 5 as shown in FIG. 4A.

To further demonstrate library screening, $1\times10^8$ phage from the mouse genomic λKO-1 library were infected into $2\times10^9$ SCRN10(pML184) cells and amplified as described above. $3\times10^{11}$ phage were recovered from the amplified library and $2\times10^{10}$ were infected into an equal number of BNN132 cells for automatic subcloning as previously described (Elledge et al., 1991). From these phage 327 A$^R$Tc$^R$ colonies were recovered and 48 clones were analyzed (FIG. 4B). By restriction analysis, 47 of 48 of these clones shared restriction fragments. Analysis of 48 colonies by restriction analysis and Southern blotting indicated that 47 were correct homologous recombinants representing 12 distinct genomic clones containing the target sequence. These recombinants were also shown to have picked up the homologous genomic sequences by Southern blotting with a probe to the 3.7 kB HindIII fragment containing exon 5 (See FIG. 4B). No DNA present on the targeting plasmid pML184 used to select these genomic clones is homologous to DNA on the 3.7 kB fragment. Therefore, any restriction fragment that lights up on the Southern blot represents DNA from the PTTG genomic locus that is adjacent to the region of homology used to select the genomic fragment. In all, 47 of 48 clones contained DNA homologous to the exon 5 probe. Twenty eight of the clones contained the entire 3.7 kB fragment. Nineteen clones contained part of the 3.7 kB fragment. Only one clone failed to hybridize with this fragment. That only one clone failed to show homology indicates that the frequency of non-homologous recombination under these conditions is very low. Furthermore, the isolation of 300 recombinant phage is 10-fold higher than predicted from the control experiment performed with the PTTG containing phage.

The general applicability of this method was demonstrated by screening the mouse library for two other genes, including the p57 KIP2 gene. Oligonucleotides of 70 bp in length were synthesized and these were ligated to the EcoRI and BglII sites flanking the 1.4 kB Tc$^R$ gene containing fragment. The 5' end homology corresponded to the 5' UTR region of exon 1 of p57 and the 3' end 70 bp homology region corresponded to DNA in the second intron and exon 2 of p57. The resulting fragment was cloned into the PmeI site of pML179 to create pML194 and was introduced into SCRN10 cells. The genomic library in λKO-1 was amplified on this strain as described above and the resulting phage stock was converted to plasmid form by infection into BNN132 cells selecting for Tc$^R$Ap$^R$ colonies. Twenty four clones were analyzed and found to represent 9 different phage, all but 2 of which clearly contained genomic p57 DNA as shown by restriction analysis. The observed recombination frequency was similar to that obtained in the screen using the pML184 plasmid with the PTTG gene.

Figure 8A:
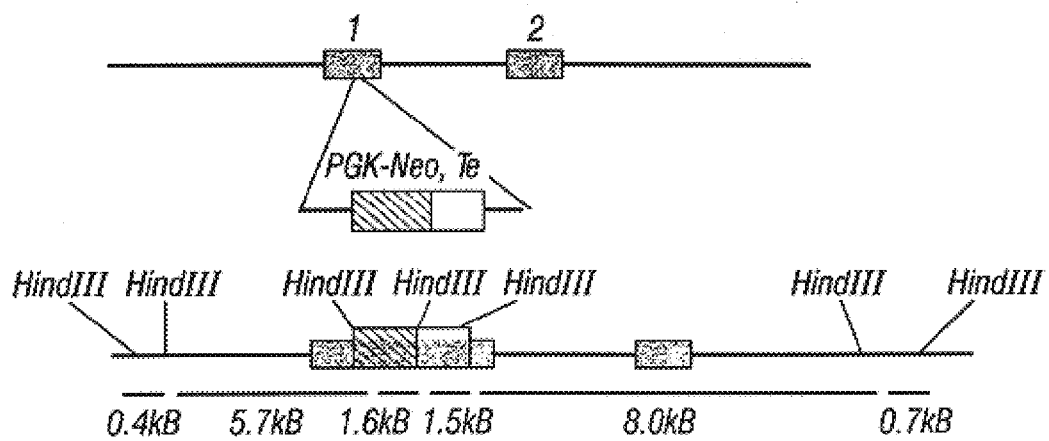
FIG. 8A is a schematic diagram illustrating the insertion of prokaryotic and eukaryotic selection markers into exon 1 of the mouse Tribbles locus. The HindIII sites used for confirmation of the homologous recombination event are also shown.
Figure 8B:
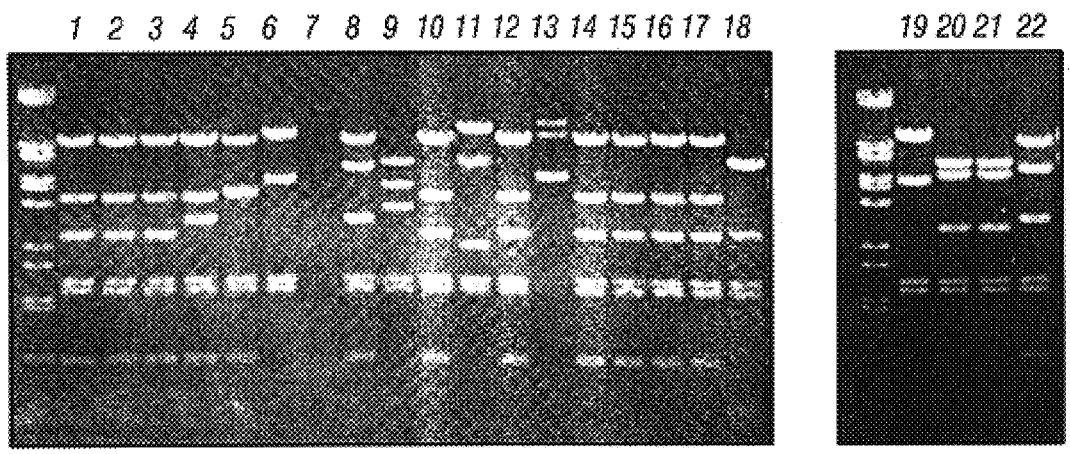
FIG. 8B is data from a HindIII restriction enzyme digestion of homologous plasmids selected by recombination library screening that results in an insertion into exon 1 of the mouse Tribbles locus as depicted in FIG. 8A. The DNA in lanes 1–3, 10, 12, and 14–17 includes expected bands of 0.7, 1.5, 1.6, and 8 kB. Lanes 20 and 21 are examples of DNA containing expected fragments of 0.4, 1.5, 1.6, and 5.7 kB.

The third gene used for targeting was the mouse homologue of the drosophila tribbles gene involved in cell cycle control. In this case an insertion allele was generated by inserting a restriction fragment containing the PGK-Neo and Tc$^R$ genes into the BamHI site in the first exon of the mouse Tribbles gene (FIG. 8). The PGK-Neo gene can be used to select for homologous recombination in ES cells. This fragment was excised from the Tribbles cDNA fragment by SmaI digestion and cloned into the targeting vector pML179 to generate pML193. pML193 was introduced into SCRN 10 cells and the λKO-1 library was amplified on the strain as described and the resulting amplified phage stock were converted to plasmid by infection into BNN132 cells and selected for Tc$^R$Ap$^R$ colonies. Twenty two clones were analyzed and found to represent 5 different phage, all of which contained genomic Tribbles DNA. The recombination efficiency in this case was reduced by 5-fold relative to the p57 and PTTG results. The resulting plasmids containing PGK-Neo were competent for making Tribbles disruptions in ES cells. This result demonstrates that genomic library screening and targeting constructs can be made in a single step using this in vivo recombination method.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of screening a DNA library for a gene of interest comprising:
   obtaining a DNA library containing said gene of interest;
   obtaining a nucleic acid fragment that encodes a bacterial positive selection marker flanked by DNA fragments, wherein said DNA fragments are homologous with respective sequences contained in said gene of interest;
   co-transforming a host cell with a representative portion of said library and said nucleic acid fragment, wherein said host cell is an *E. coli* cell that expresses the exo and beta recombination functions of bacteriophage λ;
   incubating said host cell under conditions effective to allow said fragment to recombine into said gene of interest in said library; and
   growing said host cells under selective conditions to identify recombination events.

2. The method of claim 1, further comprising isolating a clone from the selected host cell.

3. The method of claim 1, wherein said library is a cDNA library.

4. The method of claim 1, wherein said library is a genomic library.

5. The method of claim 1, wherein said library is an animal, plant, fungal, bacterial, or yeast library.

6. The method of claim 1, wherein said library is a mammalian, insect, bacteria, plant, fish, mouse, rat, human, primate, bovine, ovine, feline, canine, porcine, guinea pig, rabbit, hamster, Drosophila, *Caenorhabditis elegans*, Arabidopsis, corn, wheat, rye, rice, or avian DNA library.

7. The method of claim 1, wherein said library is a mammalian genomic library.

8. The method of claim 1, wherein said library is a mouse genomic library.

9. The method of claim 1, wherein said library is a human genomic library.

10. The method of claim 1, wherein one or more of said exo and beta recombination functions are expressed from a plasmid in said host cell.

11. The method of claim 1, wherein said cell expresses recA.

12. The method of claim 1, wherein said cell expresses the gam recombination function.

13. The method of claim 1, wherein one or more of said exo and beta recombination functions are integrated into the genome of said host cell.

14. The method of claim 1, wherein one or more of said exo and beta recombination functions are expressed from a regulated promoter.

15. The method of claim 1, wherein one or more of said exo and beta recombination functions are expressed from an inducible or conditional promoter.

16. The method of claim 15 wherein said promoter is the lacZ promoter.

17. The method of claim 15, wherein said promoter is the tac promoter.

18. The method of claim 1, wherein said DNA fragments flanking the bacterial positive selection marker are homologous with respective sequences of about 29 or more bases in length contained in said gene of interest.

19. The method of claim 1, wherein said DNA fragments flanking the bacterial positive selection marker are homologous with respective sequences of about 50 or more bases in length contained in said gene of interest.

20. The method of claim 1, wherein said bacterial positive selection marker encodes resistance to a bacterial antibiotic.

21. The method of claim 1, wherein said positive selection marker encodes resistance to ampicillin, tetracycline, streptomycin, penicillin, chloramphenicol or neomycin.

22. The method of claim 1, wherein said library expresses a second bacterial positive selection marker.

23. The method of claim 1, wherein said library expresses a gene encoding resistance to a bacterial antibiotic.

24. The method of claim 1, wherein said bacterial positive selection marker encodes resistance to a first bacterial antibiotic and said DNA library encodes resistance to a second bacterial antibiotic.

25. The method of claim 1, further comprising providing a eukaryotic positive selection marker adjacent said bacterial positive selection marker in said fragment.

26. The method of claim 1, wherein said fragment is contained in a plasmid and wherein said method comprises transforming said host cell with said plasmid;
wherein said fragment is flanked by restriction sites that are recognized by a restriction enzyme that is expressed by the host cell under the control of an inducible promoter; and
wherein said method further comprises inducing the expression of said restriction enzyme prior to incubating said host cell under conditions effective to allow said fragment to recombine into said library.

27. The method of claim 26, wherein said restriction enzyme is I-SceI.

28. The method of claim 1, wherein said library is constructed with a vector comprising:
a lambda left arm segment;
a recombination site;
a multicloning site containing a plurality of restriction endonuclease recognition sequences;
a stuffer fragment, wherein said stuffer fragment encodes a lambda gene under the control of a constitutive promoter, the expression of which interferes with bacteriophage λ propagation;
a second multicloning site containing a plurality of restriction endonuclease recognition sequences;
a bacterial positive selection marker;
a bacterial origin of replication;
a direct repeat of said recombination site and;
a lambda right arm segment;
and wherein the library is constructed by:
removal of said stuffer fragment by endonuclease digestion;
ligation of said digested vector in the presence of fragments of DNA that encode the library sequences;
amplification of plaque forming units;
infection of E. coli host cell wherein said host cell expresses a site specific recombinase gene product effective to convert said library to plasmid form.

29. The method of claim 28, wherein said recombination site is loxP, loxP2, loxP23, loxP3, loxP511, loxB, loxC2, loxL, loxR, loxΔ86, lox117, frt, dif, RS or att.

30. The method of claim 28, wherein said stuffer fragment encodes the lambda cI gene under the control of a strong constitutive promoter.

31. The method of claim 30, wherein said strong constitutive promoter is the Con I promoter.

32. The method of claim 28, wherein said vector further comprises a negative selection marker under the operative control of a promoter, effective to act as a negative selection in a eukaryotic host cell, or a color marker effective to act as a positive selection marker in a eukaryotic host cell.

33. The method of claim 32, wherein said negative selection marker encodes herpes virus thymidine kinase.

34. The method of claim 32, wherein said color marker is GFP, luciferase or lacZ.

35. A method of obtaining a targeting vector for use in producing a mammalian embryonic stem cell with a disrupted gene of interest effective for producing a knock out mammal, said method comprising:
obtaining a DNA library comprising said gene of interest of said mammal;
obtaining a nucleic acid fragment that encodes a bacterial positive selection marker and a eukaryotic positive selection marker flanked by DNA fragments, wherein said DNA fragments are homologous with respective sequences contained in said gene of interest;
co-transforming a host cell with said library and with said nucleic acid fragment, wherein said host cell is an E. coli cell that expresses the exo and beta recombination functions of bacteriophage λ;
incubating said transformed host cell under conditions effective to allow homologous recombination between said library and said fragment such that the selection marker is transferred into the library vector;
incubating said host cell in a selective medium to select recombination events; and
isolating a clone from the selected cell,
wherein the clone is a genetic targeting vector.

36. The method of claim 35, wherein either the exo or beta recombination functions or both are expressed from a plasmid in said host cell.

37. The method of claim 35, wherein either the exo or beta recombination functions or both are expressed from the genome of said host cell.

38. The method of claim 35, wherein either the exo or beta recombination functions or both are expressed from an inducible or conditional promoter.

39. The method of claim 38 wherein said promoter is the lacZ promoter.

40. The method of claim 35, wherein said DNA fragments flanking the bacterial positive selection marker and the eukaryotic positive selection marker are homologous with respective sequences of about 30 bases or more contained in said gene of interest.

41. The method of claim 35, wherein said DNA fragments flanking the bacterial positive selection marker and the eukaryotic positive selection marker are homologous with respective sequences of about 50 bases or more contained in said gene of interest.

42. The method of claim 35, wherein said mammal is a rat, mouse, hamster, primate, bovine, ovine, feline, canine, porcine, rabbit, or guinea pig.

43. The method of claim 35, wherein said fragment is contained in a plasmid and wherein said method comprises transforming said host cell with said plasmid;

wherein said fragment is flanked by restriction sites that are recognized by a restriction enzyme that is expressed by the host cell.

44. The method of claim 43, wherein said restriction enzyme is expressed under the control of a constitutive promoter.

45. The method of claim 43, wherein said restriction enzyme is expressed under the control of an inducible promoter; and wherein said method further comprises inducing the expression of said restriction enzyme.

46. The method of claim 43, wherein said restriction enzyme is I-SceI.

47. A method of screening a library for a selected nucleic acid sequence comprising:

inserting a selectable marker into the library at the position of the selected sequence by homologous recombination in a bacterial cell, wherein said cell expresses an enhanced recombination function that is not contained on the library phage;

incubating said cell under selection conditions in order to identify a recombination event; and isolating a clone from the selected cell.

48. The method of claim 47, wherein said bacterial cell is an *E. coli* cell.

49. The method of claim 47, wherein said enhanced recombination function is a phage recombination function.

50. The method of claim 49, wherein said phage recombination function comprises the exo and beta recombination functions of bacteriophage $\lambda$.

51. The method of claim 48, wherein said library is genomic, cDNA, BAC, or cosmid library.

* * * * *